United States Patent [19]

Peart

[11] Patent Number: 5,189,264
[45] Date of Patent: Feb. 23, 1993

[54] BINAURAL STETHOSCOPE SPRING
[75] Inventor: Edward L. Peart, Arden, N.C.
[73] Assignee: Welch Allyn, Inc., Skaneateles Falls, N.Y.
[21] Appl. No.: 582,243
[22] Filed: Sep. 14, 1990
[51] Int. Cl.⁵ .................................................. A61B 7/02
[52] U.S. Cl. .................................................. 181/131
[58] Field of Search ............. 181/130, 131, 132, 133, 181/134, 135, 136, 137

[56] References Cited

U.S. PATENT DOCUMENTS

| | | | |
|---|---|---|---|
| 3,086,610 | 4/1963 | Haas | 181/131 |
| 3,108,652 | 10/1963 | Littmann | 181/132 |
| 3,275,099 | 9/1966 | Speelman | 181/132 |
| 3,295,631 | 1/1967 | Machlup | 181/131 |
| 3,437,172 | 4/1969 | Allen | 181/131 |
| 3,504,760 | 4/1970 | Littmann | 181/131 |
| 3,663,704 | 1/1972 | Ziegler et al. | 181/131 |
| 3,708,034 | 11/1973 | Ziegler et al. | 181/131 |
| 3,730,290 | 5/1973 | Scanlon | 181/131 |
| 4,200,169 | 4/1980 | MacDonald, III et al. | 181/131 |
| 4,347,911 | 9/1982 | Bertagna et al. | 181/130 |
| 4,770,270 | 9/1988 | Grimm | 181/137 |

Primary Examiner—Michael L. Gellner
Assistant Examiner—Khanh Dang
Attorney, Agent, or Firm—Wall and Roehrig

[57] ABSTRACT

An improved multi-leaf spring assembly is provided that permits greater flexibility and smoother, smaller folding of a stethoscope without deforming an individual user's adjustment. The spring leaves are held together at the ends by a spring clip. A cylindrical ferrule at each end of one leaf snaps into a groove in the lower end of an ear tube and is secured against removal by a spring clip. The entire assembly is encapsulated in an elastomer material to maintain the assembled parts in position while allowing swiveling of the ear tubes.

7 Claims, 2 Drawing Sheets 5,189,264

BINAURAL STETHOSCOPE SPRING

FIELD OF INVENTION

This invention relates to stethoscopes, and more particularly to a multiple leaf spring construction for a binaural stethoscope.

BACKGROUND OF THE INVENTION

Medical stethoscopes generally consist of a chestpiece for picking up sounds and a pair of ear tubes connected to the chestpiece, usually through separate passageways, for transmitting the sounds to each ear. The ear tubes have traditionally consisted of bent metal tubes with plastic or cushioned earplugs on the end for comfort of the wearer and insulation of outside sound sources, together with a tensioning device such as a leaf spring for maintaining the earpieces in contact with the ears of the user. Stethoscopes of this general type are illustrated in U.S. Pat. Nos. such as 3,108,652 and 4,200,169.

Various of the prior art patents have shown leaf spring constructions for joining together the bottom ends of earpieces so as to urge the curved ends into proper position in the user's ear. These have generally involved a rather wide flat leaf spring, sometimes with several leaves, with the ends of the spring formed into a semi-tubular configuration to receive the end of the ear tube. Some show the spring being crimped to the end of the ear tube inside a bushing or similar holding mechanism for joining the spring to the earpieces. The prior art devices have generally been satisfactory, but have been somewhat bulky and hard to fold for easy placing in the pocket of a doctor/user. This has been particularly true with the large single leaf springs while the multiple leaf springs have generally required a tubular bushing or other connector means to join the spring leaves to the ear tubes with consequent higher costs and difficulty of manufacture.

OBJECTS AND SUMMARY OF THE INVENTION

It is therefore an object of the present invention to provide a spring construction that overcomes the deficiencies of the prior art.

It is another object of the present invention to provide a spring construction for swiveling binaural stethoscopes which simply and easily is engaged about the lower end of the ear tube in a compact and flexible manner.

It is another object of the present invention to provide a spring construction for swiveling binaural stethoscopes that can be simply and easily manufactured in an economical fashion and that will provide improved convenience and utility for the user.

It is a further object of the present invention to provide a spring construction for a swiveling binaural stethoscope having longer spring life, positive friction control of the swiveling and better fit and resistance to damage from placement in folded condition in a pocket.

It is still a further object of the present invention to provide a spring construction that permits a more compact and aesthetically pleasing binaural stethoscope construction while maintaining superior acoustical properties.

In a preferred embodiment of the present invention, this is accomplished by forming the ends of a leaf spring into a partial cylindrical spring clip to receive an ear tube grooved end, holding at least two other leaf springs in close physical contact with the first spring leaf by a spring clip about the ends thereof forming a second spring clip to enclose the open end of the partial cylindrical spring clip, and encapsulating the assembly in a flexible plastic material to hold the spring clips and ear tube ends in assembled configuration. The ear tubes' grooved lower ends are inserted into the cylindrical receptacle formed by the end of the leaf spring and the spring clip with the ear tube ends extending therethrough so they can be inserted into the audio tube connected to the chestpiece.

BRIEF DESCRIPTION OF THE DRAWINGS

Further objects of the invention, together with additional features and advantages accruing therefrom will be apparent from the following description of a preferred embodiment shown in the accompanying drawings in which.

DETAILED DESCRIPTION OF A PREFERRED EMBODIMENT

Figure 1:
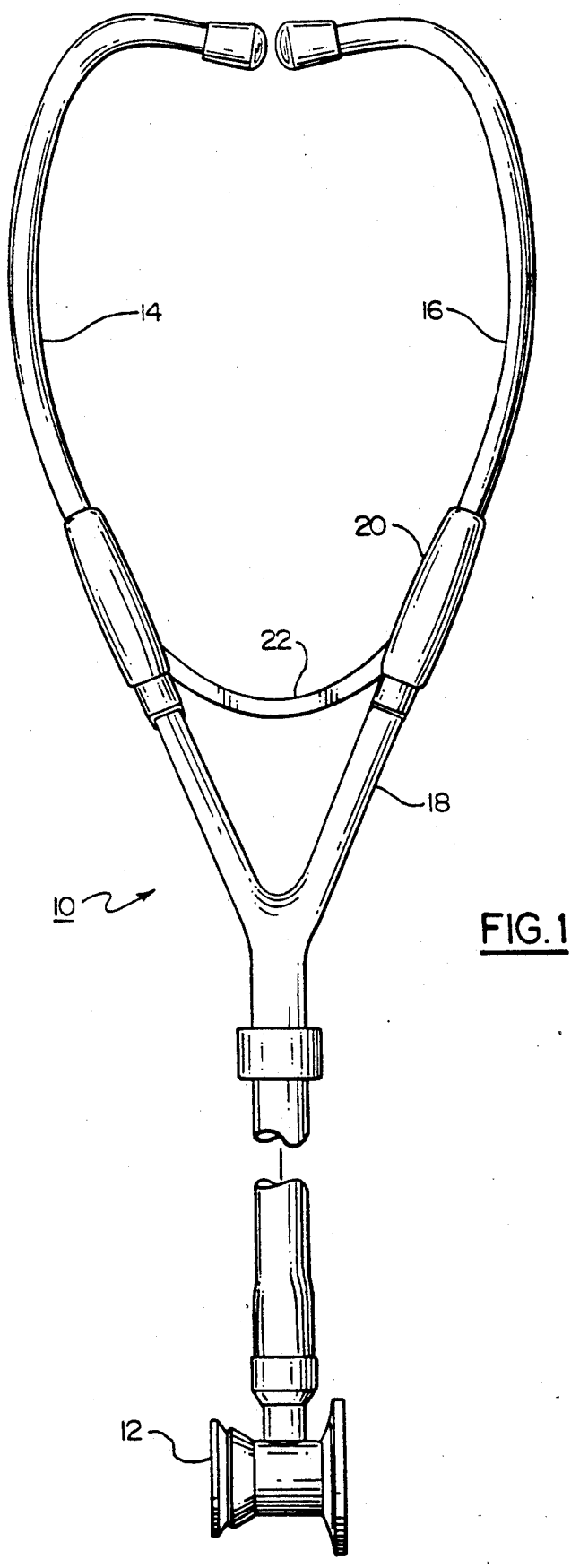
FIG. 1 is a plan view of a binaural stethoscope with a spring, according to the present invention.

Referring now to FIG. 1, there is shown a typical binaural stethoscope 10 having a chestpiece 12 and a pair of ear tubes 14 and 16, both joined to a flexible "Y" tube 18. The ear pieces and "Y" tube are joined together by the spring assembly 20, as will be described in detail herein. The "Y" tube 18 generally has two separate acoustical channels, one leading from each ear piece directly to the chestpiece 12, as is well known in the art.

The spring assembly 20 consists of a spring portion 22 having ferrules or ear tube receptacle portions 24 at each end thereof adapted to receive therein the lower end of an ear tube 14 or 16, as the case may be. The entire spring assembly is encapsulated in an elastomer coating 26 to maintain the various pieces in assembled relation to each other and to form a suitable swiveling type receptacle, together with the ferrule 24 for the end of the ear tube.

Figures 2, 3:
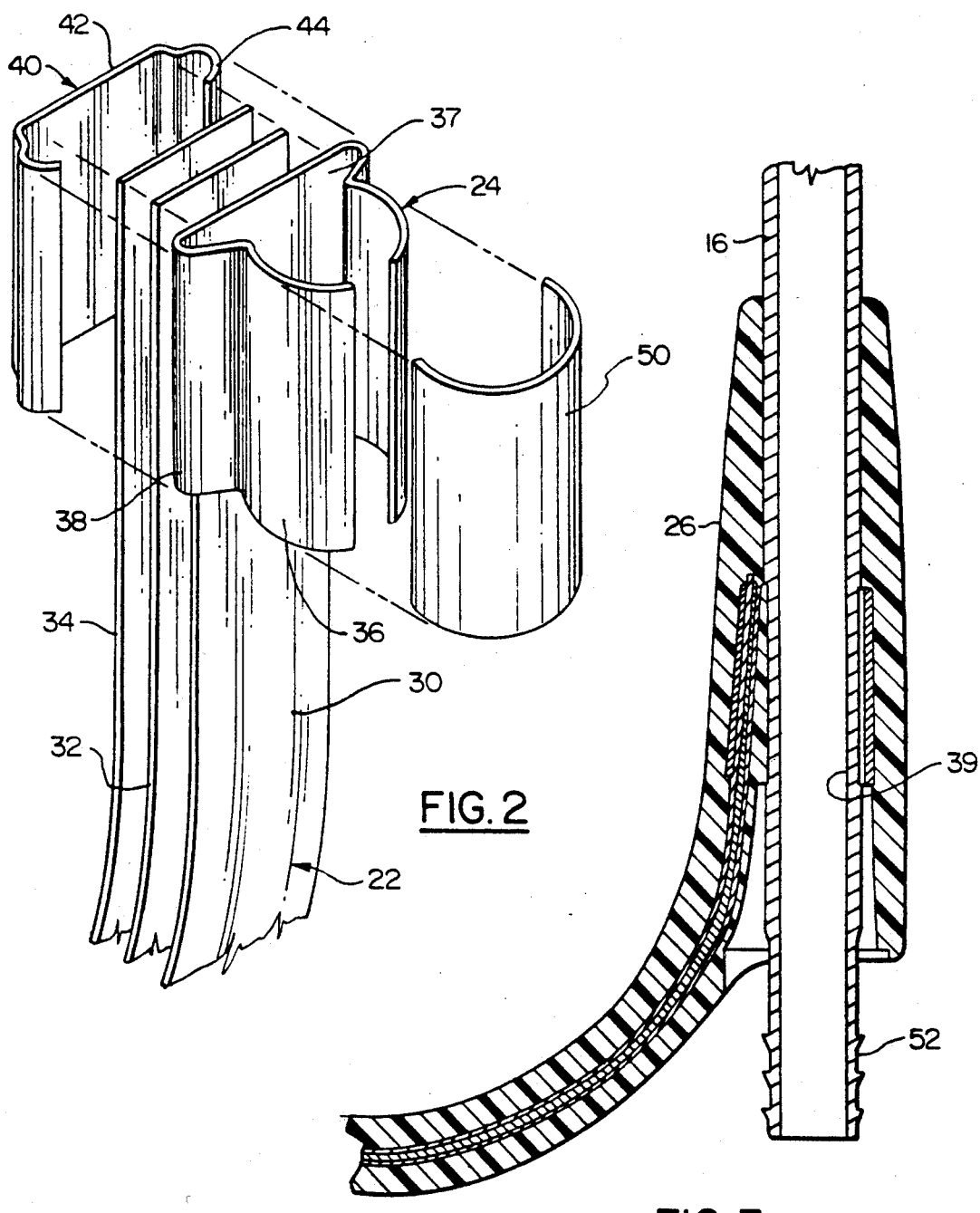
FIG. 2 is an exploded perspective view of one end of the spring in accordance with the present invention.
FIG. 3 is a cross sectional view of the spring end showing the end of an ear tube fixed therein.

As may be seen in FIGS. 2 and 3, the spring portion 22 comprises three flat spring members 30, 32 and 34 preformed into a generally U-shaped configuration and sized so as to nest one within the other to form a compact yet resilient spring member for urging opposed ends of the ear tubes together so as to securely position the stethoscope in the ears of the user. Spring 30 has at each end thereof a portion formed into a partial cylindrical receptacle or ferrule 24 which is configured to form the inner portion of a receptacle for the ear tube end. As may be seen in FIG. 2, the ferrule 24 is formed with a pair of partial cylindrical tab portions 36 integrally formed to project outwardly of the "U" of the flat leaf spring itself. Tabs 36 are joined to base portion 37 by opposed nose portions 38 giving added resilience to the cylindrical portions 36. The end of spring 30 is thus formed generally into a shape somewhat like that of a typical broom holder for gripping a cylindrical member inserted therein. The ferrule 24 being formed on the outward side of the U-shaped cross section spring 30, projects outwardly therefrom, so as to conveniently receive a pair of ear tubes therein and bias them together in the usual stethoscope fashion. Ear tubes 14 and 16 have at the lower ends a groove 39 sized to receive the tabs 36 and lock the tube therein against longitudinal removal while permitting swiveling.

The leaf spring 30 is shown as a narrow thin leaf spring member which extends from one side of the "Y" tube 18 to the other with a receptacle/ferrule portion 24 formed in each end for receiving the end of the ear tube. Second and third leaf spring members 32 and 34 are configured similarly to leaf 30, having the same approximate width and length and being pre-stressed to the same "U" shaped cross section so that they will nest one within the other. The three springs allow a narrow construction while still offering the necessary spring resilience to properly hold the stethoscope securely in the user's ears and resist deformation when placed in a pocket. This permits not only a very flexible functional unit, but also a more aesthetically pleasing unit since the narrow elongated multiple layer spring can be readily encapsulated in a plastic or elastomer covering for attractive packaging without imparing the functional aspects of the stethoscopes.

In order to secure the three springs 30, 32 and 34 together, a spring clip 40 formed generally in the same configuration as the base of the ferrule 24, but having sufficient depth to embrace and capture the ends of the springs 32 and 34 against the ferrule bottom 37 of the leaf spring 30. As may be seen in FIG. 2, the clip 40 has a flat base 42 and a pair of upstanding curved nose portions 44 which are configured to snugly fit about the curved nose portions 38 of the ferrule 24, and to snap around the noses 38 of the ferrule 24 to hold the free ends of the spring leaves 32 and 34 in intimate contact with the end of spring 30. This may be seen in cross section also in FIG. 3.

With the three springs 30, 32, and 34 mechanically held together in this fashion at each end, the additional resilience of the spring members is provided to the device while still allowing relative movement, one between the other so that maximum adjustability and convenient folding of the stethoscope are possible.

To complete the receptacle portion of the ferrule 24, a second spring clip 50 is provided in the form of a partial cylinder which is sized and shaped to snap over the cylindrical tabs 36 of the ferrule 24 and is generally disposed about the open end or space between the two tabs 36 of the ferrule 24. The spring clip 50 is snapped into position about the tabs 36, after insertion of the grooved ends of ear tubes 14 and 16, but is not fixed thereto so that additional spring force can be imparted to ferrule 24 to hold it in the groove 39 and further secure tubes 14 and 16 in the receptacle formed by the ferrule 24 and the clip 50.

The springs 30, 32, 34 and clips 40 and 50, when assembled, are encapsulated within an elastomer coating 26 which is generally of a flexible but stiff plastic material so as to form a housing for the spring assembly 20 and the ends of the ear tubes 14 and 16 respectively, while still allowing swiveling of the tubes therein.

With the spring clip 40 positioned about the ferrule 24 and the three leaf springs 30, 32, and 34, assembled together, a unitary spring is formed which will tend to urge any ear tubes inserted in the ferrules 24, together in overlapping relation, as is customary. As may be seen in FIG. 3, in the encapsulated assembly the barbed end 52 of the ear tube 16 extends out of the encapsulated ferrule for connection to the "Y" tube 18. The upper end of the "Y" tube is forced over the bayonet or barbed end 52 of the ear tubes 14 and 16 to form the stethoscope as shown in FIG. 1.

Tubes 14 and 16 can thus be rotated within the ferrule 24 and the enclosing sheath of elastomer material 26 by turning the ear tube to the desired angular relationship with the spring and the "Y" tube upper end and the friction of the ferrule and clips will hold them in the desired position. In this way, the stethoscope can be adjusted for the preferred fit for the user.

With the multiple leaf narrow spring assembly 22, not only is the aesthetic appearance of the spring member across the face of the stethoscope more pleasing because it is smaller and trimmer, but the three leaf spring member gives greater flexibility, and a more uniform force resisting deflection. Since the individual leaf spring members can slide relative one to the other and since the ear tubes can be rotated within the spring assembly ferrules there is less accidental damage when folded and placed in a pocket. The stethoscope can be adjusted for the maximum possible convenience of the user and also for folding into a small unobtrusive package for placing in one's pocket. The smaller width spring is much easier to insert and withdraw from a pocket for physicians or other users who are usually very busy and appreciate simplicity and reliability of a product they must use constantly. Also, the construction shown provides a rugged, long lasting, low maintenance device for the user.

While this invention has been explained with reference to the structure disclosed herein, it is not confined to the details as set forth and this application is intended to cover any modifications and changes as may come within the scope of the following claims.

What is claimed is:

1. In a stethoscope having a pair of elongated ear tubes each having an upper end suitably curved for insertion into an ear of a wearer, and lower end suitable for connection to a flexible "Y" tube connected to a chestpiece, a U-shaped spring assembly having two ends for joining the lower ends of said ear tubes and biasing the curved upper ends thereof toward each other which comprises:
   a first leaf spring formed into a generally U-shaped configuration having at each end thereof a partial cylindrical ferrule extending outwardly of the U-shape thereof and adapted to engage in a cooperating groove in the ear tube lower end;
   second and third leaf springs formed into a generally U-shaped configuration corresponding to that of said first leaf spring so as to nest therein;
   said second and third leaf springs being positioned on an inner surface of the U-shaped first leaf spring and extending from end to end thereof; and
   at each end of said spring assembly:
   a first spring clip member open on one side, adapted to be snapped about said partial cylindrical ferrule from the inner surface of the U-shaped spring assembly to secure the end of said second and third leaf springs to the end of said first leaf spring;
   a second spring clip member open on one side adapted to be engaged about a cylindrical portion of said partial cylindrical ferrule to lock said ferrule in the cooperating groove in the ear tube lower end; said ferrule and second spring clip member together forming a receptacle for receiving a grooved lower end of the ear tube to allow swiveling of the ear tube relative to the "Y" tube and spring assembly, but prevent withdrawal therefrom when fully assembled; and an elastomer coating encapsulating said first, second, and third leaf springs, said ferrule, and said first and second spring clip members to maintain them in assembled form about the lower end of the ear tube to be joined to a flexible "Y" tube and chespiece to constitute a stethoscope.

2. A stethoscope spring assembly in accordance with claim 1 wherein said ferrule, said first and second spring clip member, and said leaf first, second, and third leaf springs, when encapsulated in an elastomer coating, are still free to move relative to each other upon flexing of the spring assembly and rotation of the ear piece ends in the formed receptacle whereby a stethoscope so formed is extremely flexible and easily folded for pocket storage without changing adjustment, yet has excellent acoustic characteristics.

3. A stethoscope spring assembly according to claim 1 wherein the partial cylindrical ferrule on each end of said first leaf spring comprises:
- a flat base portion extending laterally beyond the width of the first leaf spring;
- a pair of partial cylindrical tabs extending outwardly from the first leaf spring in a generally perpendicular relation thereto; and
- a pair of curved nose members joining said tabs to said base portion whereby a strong spring receptacle is formed for an ear tube end.

4. A stethoscope spring assembly according to claim 3 wherein said first spring clip member has a base portion, and a pair of nose members extending therefrom and adapted to fit over and conform to the corresponding nose members of the partial cylcindrical ferrule so as to hold said second and third leaf springs in mating alignment with said first leaf spring.

5. A stethoscope according to claim 4 wherein said second spring clip member comprises a partial cylindrical body having a generally "C" shaped cross-section and a length equal to the length of the partial cylindrical ferrule.

6. A stethoscope having a chestpiece;
- a pair of elongated ear tubes each having an upper end suitably curved for insertion into the ear of a wearer, and a lower end suitable for connection to a flexible tube;
- an annular groove adjacent the lower end of each ear tube; a flexible "y" tube connected from said chestpiece to the lower ends of the ear tubes; a spring assembly having two ends connecting the lower ends of said ear tubes and biasing the curved upper ends toward each other including:
- a first leaf spring formed into a generally U-shaped configuration having at each end thereof a partial cylindrical ferrule having an outwardly extending portion extending outwardly of the U-shape and adapted to engage in said annular groove in the ear tube lower end;
- second and third leaf springs nested in said first leaf spring and extending from end to end thereof;
- a first clip member open on one side, adapted to be snapped about said cylindrical ferrule from an inner surface of the U-shaped spring assembly to secure the ends of said second and third leaf springs to the end of said first leaf spring;
- a second clip member open on one side adapted to be engaged about a cylindrical portion of said partial cylindrical ferrule to lock said ferrule in said groove in the ear tube lower ends;
- at each end of said spring assembly first, second, and elastomer coating encapsulating said leaf springs and first and second, spring clip members to maintain them in assembled form about the lower end of the ear tube joined to the flexible "Y" tube and chestpiece.

7. In a stethoscope having a pair of elongated ear tubes each having an upper end suitably curved for insertion into an ear of a wearer, and a lower end suitable for connection to a flexible "Y" tube connected to a chestpiece, a U-shaped spring assembly having two ends for joining the lower ends of said ear tubes and biasing the curved upper ends thereof toward each other with comprises:
- a first leaf spring formed into a generally U-shaped configuration having at each end thereof a partial cylindrical ferrule extending outwardly of the U-shaped and adapted to engage in a cooperating groove in the ear tube lower end;
- an additional leaf spring formed into a generally U-shaped configuration corresponding to that of said first leaf spring so as to nest therein;
- said additional leaf spring being positioned on an inner surface of the U-shaped first leaf spring and extending from end to end thereof; and
- at each end of said spring assembly:
- a first spring clip means formed to snap about said partial cylindrical ferrules from an inner surface of the U-shaped spring assembly to secure the end of said additional leaf spring to the end of said first leaf spring;
- a second spring clip means formed to engage about a cylindrical portion of said partial cylindrical ferrule to lock said ferrule in a cooperating groove in the ear tube lower ends;
- said ferrule and second spring clip means together forming a receptacle for receiving the grooved lower end of the ear tube to allow swiveling of the ear tube relative to the "Y" tube and spring assembly, but prevent withdrawal of said ear tube therefrom when said stethoscope is fully assembled; and
- an elastomer coating encapsulating said leaf springs and first and second spring clip means to maintain them in assembled form about the lower end of the ear tube to be joined to a flexible "Y" tube and chestpiece to constitute a stethoscope.

* * * * *